United States Patent [19]

Whalen et al.

[11] Patent Number: 4,772,593
[45] Date of Patent: Sep. 20, 1988

[54] ALKOXYSILANE COMPOUNDS IN THE TREATMENT OF SWINE DYSENTERY

[75] Inventors: Joseph W. Whalen; Edward E. Flagg, both of Midland, Mich.

[73] Assignee: The Dow Chemical Company, Midland, Mich.

[21] Appl. No.: 750,615

[22] Filed: Jul. 1, 1985

[51] Int. Cl.$^4$ ............................................. A61K 31/695
[52] U.S. Cl. ....................................................... 514/63
[58] Field of Search .............................................. 514/63

[56] References Cited

U.S. PATENT DOCUMENTS

| | | | |
|---|---|---|---|
| 3,011,943 | 12/1961 | Rogers et al. | 514/63 |
| 3,382,150 | 5/1968 | Grass, Jr. et al. | 514/63 |
| 3,730,701 | 5/1973 | Isquith et al. | 71/67 |
| 3,794,736 | 2/1974 | Abbott et al. | 514/63 |
| 4,259,103 | 3/1981 | Malek et al. | 514/63 |
| 4,282,366 | 8/1981 | Eudy | 71/67 |
| 4,394,378 | 7/1983 | Klein | 71/67 |

OTHER PUBLICATIONS

Dow Corning 5700 Antimicrobial Agent, product information, 1976.
Isquith et al. "Surface-Bonded Antimicrobial Activity of an Organosilicon Ammonium Chloride", Appl. Micro., 24, 859–863, 1972.
Kinyon et al. 2nd Int'l Symposium of Veterinary Laboratory Diagnosticians, Lucerne, Switzerland, pp. 125–128, 1980.
Walters et al. "Algicidal Activity of a Surface-Bonded Organosilicon Quaternary Ammonium Chloride", Appl. Micro., 25, 253–256, 1972.

Primary Examiner—Albert T. Meyers
Assistant Examiner—John M. Kilcoyne
Attorney, Agent, or Firm—Thomas R. Savitsky; Ronald G. Brookens

[57] ABSTRACT

The invention discloses a method of treating swine dysentery by the administration of an animal feed composition containing an effective amount of an alkoxysilane compound such as 3-(triethoxysilyl)propyloctadecyldimethyl ammonium chloride.

42 Claims, No Drawings

ALKOXYSILANE COMPOUNDS IN THE TREATMENT OF SWINE DYSENTERY

BACKGROUND OF THE INVENTION

Swine dysentery is a severe debilitating disease of pigs estimated to cause over 70 million dollars annual loss in the United States. The economic loss is due to death of pigs, decreased growth rate of pigs, and poor feed conversion efficiency by pigs having swine dysentery, as well as expenses incurred by chemotherapy. Harris and Glock report that morbidity of swine dysentery in field cases may approach 90 percent and mortality may be as high as 30 percent. See *Diseases of Swine*, 5th Edition, p. 432 et. seq. (Iowa State University Press, 1981).

The primary causative organism of swine dysentery is *Treponema hyodysenteriae* which induces lesion formation on the large intestine. Infected pigs generally suffer from diarrhea although the severity may vary. The ultimate cause of death is usually associated with dehydration, acidosis, and hyperkalemia due to the diarrhea.

Various antimicrobials and antibiotics are currently used in treating swine dysentery, although strains of *T. hyodysenteriae* resistant to all of the presently approved therapeutics have been reported. Hence, it would be desirable to provide an effective, low dosage therapeutic which would be used in treating this economically devasting disease.

SUMMARY OF THE INVENTION

The present invention is directed to a method of treating swine dysentery in swine in need of treatment by administering to said swine an animal feed composition comprising animal feed in admixture with an effective amount of one or more compounds of the formula:

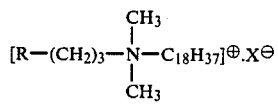

wherein R represents:

(a)

$(R^1O)_3Si-$ wherein each $R^1$ independently represents a straight or branched alkyl moiety of from 1 to 12 carbon atoms, inclusive, or a cyclic alkyl moiety of from 3 to 12 carbon atoms, inclusive, said alkyl moieties are optionally substituted with 1 to 12 hydroxyl groups and 1 to 2 amino groups;

(b)

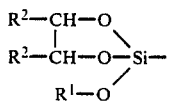

wherein each $R^2$ independently represents H or a straight or branched alkyl moiety of from 1 to 11 carbon atoms, inclusive, or a cyclic alkyl moiety of from 3 to 11 carbon atoms, inclusive, said alkyl moieties are option- ally substituted with 1 to 11 hydroxyl groups and 1 to 2 amino groups, and $R^1$ is as defined hereinabove;

(c)

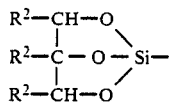

wherein $R^2$ is as defined hereinabove;

(d)

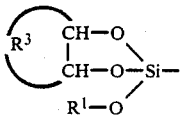

wherein $R^3$ is a straight or branched alkyl moiety of from 3 to 10 carbon atoms, inclusive, or a cyclic alkyl moiety of from 6 to 10 carbon atoms, inclusive, said alkyl moieties are optionally substituted with 1 to 10 hydroxyl groups and 1 to 2 amino groups, and $R^1$ is as defined hereinabove;

(e)

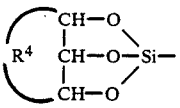

wherein $R^4$ is a straight or branched alkyl moiety of from 2 to 9 carbon atoms, inclusive, or a cyclic alkyl moiety of from 5 to 9 carbon atoms, inclusive, said alkyl moieties are optionally substituted with 1 to 9 hydroxyl groups and 1 amino group;

(f)

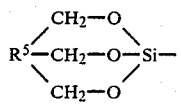

wherein $R^5$ is a straight or branched alkyl moiety of from 1 to 6 carbon atoms, inclusive, optionally substituted with 1 amino group; and $X^\ominus$ is a physiologically acceptable anion.

The compounds of formula I described above will hereinafter be referred to as the "alkoxysilane compounds".

The alkoxysilane compound used in the method of the present invention wherein $X^\ominus$ is chloride and R is $(CH_3O)_3Si-$ is commercially available from the Dow Corning Corporation, Midland, MI 48640 and has the designation of Dow Corning ® 5700 Antimicrobial Agent or, alternatively, Q9-5700.

The present invention also relates to an animal feed composition comprising a mixture of animal feed and an effective amount of one or more alkoxysilane compounds.

It has been found that a surprising level of treatment is obtained when the alkoxysilane compounds are incorporated into animal feed.

DETAILED DESCRIPTION OF THE INVENTION

The alkoxysilane compounds when admixed with animal feed are effective in the treatment of swine dysentery at low concentrations. As used herein, "treatment" of swine dysentery includes prevention and/or control of swine dysentery; "prevention" refers to prophylactic administration of the alkoxysilane compounds to presently uninfected animals which may be susceptible to the disease as, for instance, uninfected animals which are in contact with infected animals; and "control" refers to administration of said compounds to animals suffering from swine dysentery in order to ameliorate the severity of the disease or cure the disease.

As used herein, the term "effective amount" refers to that amount of one or more alkoxysilane compounds admixed with animal feed to form an animal feed composition such that when said animal feed composition is administered to swine, the desired treatment of swine dysentery is obtained. One or more alkoxysilane commpounds may be admixed with animal feed at an effective amount of from about 500 parts by weight of the compound(s) per million parts by weight of the final animal feed composition (ppm) to about 1500 ppm. A preferred effective amount is from about 600 ppm to about 1000 ppm. Typically, a lesser amount of the alkoxysilane compounds will be required to prevent the disease rather than control it. The exact amount of the alkoxysilane compounds to be admixed with the animal feed may vary depending on the species of the animal being treated, and the size, weight, and age of the animal. In addition, the severity of the disease and other stress factors will also have a bearing on the exact amount of the alkoxysilane compounds to be admixed with the animal feed. For any particular case, the exact amount to be admixed with the animal feed may be determined by conventional dose titration techniques. As used herein the term "animal feed" refers to feed which is suitable to feed to swine and which meets part or all of the swine's nutritional or growth requirements.

The $X^{\ominus}$ substituent of the compounds of formula I may be an organic or inorganic physiologically acceptable anion. Typical physiologically acceptable inorganic anions include sulfate, bisulfate, sulfite, iodide, chloride, bromide, phosphate, nitrate, and the like. Typical physiologically acceptable organic anions include acetate, propionate, benzoate, benzenesulfonate, substituted enzenesulfonate (such as p-toluenesulfonate), lactate, citrate, alkylphosphate, dialkylphosphinate, and the like.

Preferred alkoxysilane compounds for use in the present invention are those of the formula:

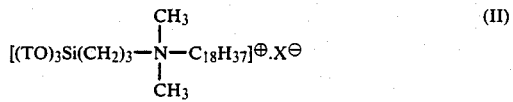
(II)

wherein each T independently represents a straight or branched alkyl moiety of from 1 to 5 carbon atoms, inclusive, or a cyclic alkyl moiety of from 3 to 5 carbon atoms, inclusive, said alkyl moieties are optionally substituted with 1 to 5 hydroxyl groups and 1 amino group; and $X^{\ominus}$ is as defined hereinabove.

Other preferred alkoxysilane compounds for use in the present invention are those of the formula:

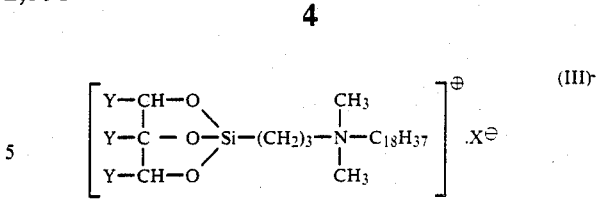
(III)

wherein each Y independently represents H, or a straight or branched alkyl moiety of from 1 to 3 carbon atoms, inclusive, optionally substituted with 1 to 3 hydroxyl groups and 1 amino group; and $X^{\ominus}$ is as defined hereinabove.

Other preferred alkoxysilane compounds for use in the present invention are those of the formula:

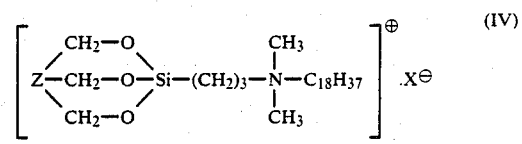
(IV)

wherein Z represents an alkyl moiety of 1 or 2 carbon atoms optionally substituted with 1 amino group; and $X^{\ominus}$ is as defined hereinabove.

The compounds of formulas I, II, III or IV wherein $X^{\ominus}$ is chloride are also preferred.

The most preferred compound is 3-(triethoxysilyl)-propyloctadecyldimethyl ammonium chloride.

Alkoxysilane compounds are well known materials which are prepared by known means; for example, by the method described in U.S. Pat. No. 3,730,701 (incorporated herein by reference).

Most of the alkoxysilane compounds used in the present invention can be conveniently made by using Dow Corning ® Q9-5700 as a starting material. The methoxysilane moieties on Dow Corning ® Q9-5700 may be substituted with other physiologically acceptable alkoxy moieties. These alkoxy moieties can be obtained from commonly available compounds whch contain a replaceable proton. Examples of such compounds are ethanol, propanol, tris(hydroxymethyl)aminomethane, xylitol, sugars such as glucose, and the like. As appreciated by one skilled in the art, the alkoxysilane compounds used in the present invention can also be prepared by other known standard methods.

The alkoxysilane compounds used in the present invention are quaternary ammonium salts. As appreciated by those skilled in the art, quaternary ammonium salts are typically inactivated when in contact with organic matter. Therefore it is a surprising and unexpected feature of the present invention that a satisfactory level of treatment of swine dysentery is obtained when the alkoxysilane compounds are incorporated into animal feed since typical animal feed is substantially organic matter.

For commercial use, it is convenient to provide a feed additive premix, mineral supplement or concentrate containing one or more of the alkoxysilane compounds in a proportion such that a predetermined quantity of the premix or concentrate may be added to a quantity of animal feed whereby an animal feed is obtained which contains an effective amount of one or more of the alkoxysilane compounds. The feed additive premix or concentrate comprises one or more alkoxysilane compounds described herein along with physiologically acceptable adjuvants and carriers such as soybean meal, ground corn, ground corn cobs, corn oil, barley, wheat or other edible feed grade material, mineral or vitamin mixtures, or an innocuous diluent such as an alcohol, a glycol or molasses.

The method of the present invention further contemplates treating swine with one of the compositions containing one or more alkoxysilane compounds described herein in combination with one or more additives such as coccidiostats, antibiotics, minerals, vitamins or any other physiologically beneficial agents employed in animal husbandry.

The following examples are set forth as a means of illustrating the present invention and are not to be construed as a limitation thereon.

EXAMPLE 1

Preparation of 3-(triethoxysilyl)-propyloctadecyldimethyl ammonium chloride.

A 42% by weight solution of 3-(trimethoxysilyl)-propyloctadecyldimethyl ammonium chloride in methanol (Q9-5700) was obtained from The Dow Corning Corporation, Midland, Mich. Approximately 148.3 grams of the solution was placed in a Rotavapor ® rotary evaporator and most of the methanol was removed. Ethyl alcohol (dry, absolute) was added slowly through the solvent feed-dip tube in the top of the Rotavapor ® rotary evaporator while the evaporation process was taking place. The solution was then evaporated almost to dryness. This process was repeated at least five times at approximately 35° C. The final product contained predominately 3-(triethoxysilyl)-propyloctadecyldimethyl ammonium chloride.

EXAMPLE 2

Preparation of 3-(tris(2-amino-2-hydroxymethyl-3-hydroxypropoxy)silyl)propyloctadecyldimethyl ammonium chloride

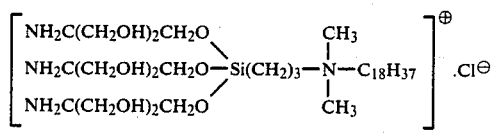

8.1 Grams of tris(hydroxymethyl)aminomethane ($NH_2C(CH_2OH)_3$) was mixed with 200 ml of dimethylformamide (DMF) in a 500 ml three neck flask and heated to 70° C. which resulted in a clear solution. A mixture of 26.3 grams of a solution of 3-(trimethoxysilyl)propyloctadecyldimethyl ammonium chloride (42% by weight in methanol) and 50 ml of DMF was added to the clear solution from a dropping funnel while maintaining the temperature at 50° C. or higher. After the addition was completed, the temperature was increased to 90° C. for approximately one hour. The mixture was cooled and transferred to a Rotavapor ® rotary evaporator where most of the DMF was removed which resulted in a yellow solid. The yellow solid was redissolved in DMF and the solvent evaporation was repeated at approximately 48° C. The resulting solid was redissolved in DMF, treated with activated carbon, then filtered through diatomaceous earth (Celite ®). The solvent was removed again and drying was completed in a vacuum oven. 13.2 Grams of solid was isolated which was predominately 3-(tris(2-amino-2-hydroxymethyl-3-hydroxypropoxy)silyl)propyloctadecyldimethyl ammonium chloride.

EXAMPLE 3

Preparation of 3-(2-amino-2-hydroxymethyl-3-hydroxypropoxysilyl)propyloctadecyldimethyl ammonium chloride

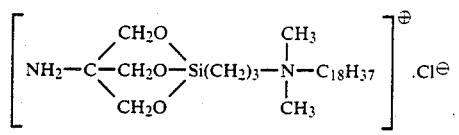

3.95 Grams of Tris(hydroxymethyl)aminomethane, approximately 250 ml of DMF, and 37.8 g of a solution of 3-(trimethoxysilyl)propyloctadecyldimethyl ammonium chloride (42% by weight in methanol) were mixed and heated at 130° C. for approximately 16 hours. After cooling, most of the DMF was removed using a Rotavapor ® rotary evaporator. More DMF was added and DMF evaporation repeated. A brownish, off-white solid was obtained after further drying in a vacuum oven at 45°-50° C. The brownish, off-white solid was soluble in hot DMF, and partially soluble in dichloromethane and chloroform. The brownish, off-white solid was dissolved in hot DMF, treated with activated carbon, then most of the DMF was removed. The activated carbon treatment was repeated using chloroform as the solvent. The resulting solution was filtered, partially evaporated and petroleum ether added. The solvents were then removed which resulted in an amorphous solid which contained a significant amount of 3-(2-amino-2-hydroxymethyl-3-hydroxypropoxysilyl)propyloctadecyldimethyl ammonium chloride.

EXAMPLE 4

Preparation of 3-((xylitoxy)silyl)propyloctadecyldimethyl ammonium chloride

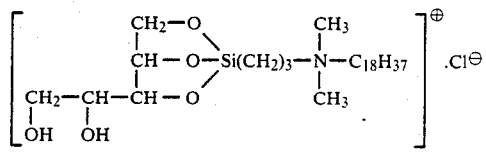

7.2 Grams of xylitol ($CH_2OH(CHOH)_3CH_2OH$), 75 ml of DMF, and approximately 22.9 g of 3-(triethoxysilyl)propyloctadecyldimethyl ammonium chloride (prepared as described in Example 1) were mixed and heated to 100° C. for approximately 4 hours, then heated overnight (approximately 16 hours) at 70°-75° C. After removing most of the DMF on a Rotavapor ® rotary evaporator the procedure was repeated which resulted in a solid. The solid was redissolved in hot DMF, treated with activated carbon and filtered. The DMF was then removed which resulted in a solid which was predominantly 3-(xylitoxy)silyl)propyloctadecyldimethyl ammonium chloride.

EXAMPLE 5

To test the in vitro activity of the alkoxysilane compounds against *T. hyodysenteriae*, the following procedure was used.

A one percent suspension of 3-triethoxysilyl)-propyloctadecyldimethyl ammonium chloride, prepared as described in Example 1, in water was made.

From the aqueous one percent suspension, 0.1% and 0.01% aqueous suspensions were made. Appropriate amounts of the two latter suspensions were incorporated into molten modified trypticase soy agar, (at about 45° C.) containing about 5% bovine blood, in order to obtain trypticase soy agars having the following concentrations of alkoxysilane compound per ml of agar: 100, 75, 50, 25, 15, 10, 5, 1.0 and 0.5 micrograms (μg) of the alkoxysilane compound per milliliter (ml). The respective agars, each containing a known concentration of the alkoxysilane compound, were each poured into individual sterile petri dishes and allowed to solidify at room temperature. Each petri dish containing the solidified agar was then inoculated with a swab containing an inoculum (approximately 0.1 ml) at a concentration of approximately $1.0 \times 10^4$ to $1.0 \times 10^5$ *T. hyodysenteriae* organisms per ml. The strain of *T. hyodysenteriae* used for the inoculation was B-78 which was originally isolated from a pig with swine dysentery. After inoculation, the petri dishes were incubated at about 41° C. for at least 6 days in an atmosphere of 50% hydrogen and 50% carbon dioxide. Following incubation, each inoculated petri dish containing a specific concentration of the alkoxysilane compound was examined for characteristic growth of *T. hyodysenteriae* and the hemolysis of the blood produced by such growth. Inoculated petri dishes containing modified trypticase soy agar with about 5% bovine blood without any alkoxysilane compound was used as a positive control for growth of *T. hyodysenteriae*. The presence of *T. hyodysenteriae* was confirmed by microscopic examination. The minimum inhibitory concentration (MIC) was the lowest concentration of the alkoxysilane compound which inhibited growth of *T. hyodysenteriae*. The MIC for 3-(triethoxysilyl)propyloctadecyldimethyl ammonium chloride was determined to be less than or equal to 0.5 μg/ml.

EXAMPLE 6

The procedure substantially as described in Example 5 was used for testing 3-(2-amino-2-hydroxymethyl-3-hydroxypropoxy silyl)propyloctadecyldimethyl ammonium chloride; and the MIC was determined to be 15 μg/ml.

inoculum used to inoculate the medium was obtained from baffled culture flasks inside Gas-Pak ® jars shaken during incubation at 37° C.

The successful infection of mice with *T. hyodysenteriae* has been reported in the literature and a similar procedure was utilized herein (see Joens and Glock, *Experimental Infection in Mice with Treponema hyodysenteriae;* Infec. Immun 25, 757–760 (1979)). Two groups of mice were infected with *Treponema hyodysenteriae* by gavage with an infecting dose at a concentration of approximately $1.0 \times 10^8$ organisms per milliliter of broth culture obtained from the cultivated strain described above. The infecting dose was 1.0 ml of said broth culture administered on two successive days (a total of 2.0 ml). In this procedure it is important that the infection of the mice be accomplished with an inoculum of about $1.0 \times 10^7$ to $1.0 \times 10^8$ organisms from a young, vigorous culture of *Treponema hyodysenteriae*. One of the groups was designated as the treatment group and was administered 3-(triethoxysilyl)propyloctadecyldimethyl ammonium chloride in the animal feed. The 3-(triethoxysilyl)propyloctadecyldimethyl ammonium chloride was prepared as described in Example 1, admixed with the animal feed, and the admixture then dried to remove excess water and ethanol. The second infected group was maintained as a non-treated control. A third group of mice was maintained as a non-infected control. Fourteen days after the mice were first infected with *Treponema hyodysenteriae*, the mice in the treatment group were administered the compound (admixed in Purina ® rodent laboratory chow) at the concentration indicated in Table 2. Throughout the procedure described herein, food and water were available ad libitum. Treatment was continued for 14 days at which time fecal pellets were collected and cultured (one culture per mouse) for the presence of *Treponema hyodysenteriae*. On days 32 and 42 following infection, mice were sacrificed. Samples from the colonic mucosa were collected and also cultured (one culture per sacrified mouse) for the presence of *Treponema hyodysenteriae*. The sacrificed mice were autopsied and examined for evidence of intestinal lesions typical of that caused by *Treponema hyodysenteriae* in swine dysentery. The results of this evaluation are shown in Table 2.

TABLE 2

| Group | Concentration of Alkoxysilane Compound Administered (ppm) | Fecal Cultures[a] | Cecal Cultures[a] | Pathology[b] | Total Number of Mice | Number of Mice Sacrificed at 32 Days | Number of Mice Sacrificed at 42 Days |
|---|---|---|---|---|---|---|---|
| Infected Control | — | 4/6 | 6/6 | 6/6 | 6 | 2 | 4 |
| Treatment | 600 | 0/3 | 0/3 | 0/3 | 3 | 1 | 2 |
| Non-infected Control | — | 0/3 | 0/3 | 0/3 | 3 | 1 | 2 |

[a]Value refers to the number of positive cultures of *Treponema hyodysenteriae* per number of total cultures.
[b]Number of animals observed with gross lesions per number of animals examined.

EXAMPLE 7

The procedure substantially as described in Example 5 is used for testing 3-(tris(2-amino-2-hydroxymethyl-3-hydroxypropoxy)silyl)propyloctadecyldimethyl ammonium chloride and 3-((xylitoxy)silyl)propyloctadecyldimethyl ammonium chloride; both compounds are antibacterially active against *T. hyodysenteriae*.

EXAMPLE 8

In order to evaluate the in vivo activity of the alkoxysilane compounds the following procedure was used.

An infecting strain of *Treponema hyodysenteriae* (strain B-78) was cultured in a liquid medium. Said medium was substantially the same as that reported by Kinyon and Harris in Vet. Rec. 95, 219–220 (1974). The From the data shown in Table 2 it is clear that the alkoxysilane compound was effective in eradicating *Treponema hyodysenteriae* from the mice. The strain of *Treponema hyodysenteriae* used in this study induced an infection in the mice similar to that manifested as swine dysentery in swine. This was confirmed by the pathological observations of the cecum and colon of the mice which had lesions similar to the lesions found in infected swine.

What is claimed is:

1. A method for treating swine dysentery in swine in need of such treatment which comprises administering to said swine an animal feed composition comprising animal feed in admixture with an effective swine dysentery treating amount of at least one of the compounds of the formula:

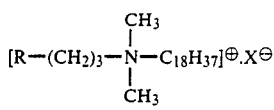

wherein R represents:

(a)

wherein each $R^1$ independently represents a straight or branched alkyl moiety of from 1 to 12 carbon atoms, inclusive, or a cyclic alkyl moiety of from 3 to 12 carbon atoms, inclusive, said alkyl moieties are optionally substituted with 1 to 12 hydroxyl groups and 1 to 2 amino groups;

(b)

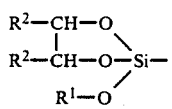

wherein each $R^2$ independently represents H or a straight or branched alkyl moiety of from 1 to 11 carbon atoms, inclusive, or a cyclic alkyl moiety of from 3 to 11 carbon atoms, inclusive, said alkyl moieties are optionally substituted with 1 to 11 hydroxyl groups and 1 to 2 amino groups, and $R^1$ is as defined hereinabove;

(c)

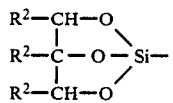

wherein $R^2$ is as defined hereinabove;

(d)

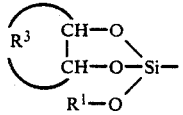

wherein $R^3$ is a straight or branched alkyl moiety of from 3 to 10 carbon atoms, inclusive, or a cyclic alkyl moiety of from 6 to 10 carbon atoms, inclusive, said alkyl moieties are optionally substituted with 1 to 10 hydroxyl groups and 1 to 2 amino groups, and $R^1$ is as defined hereinabove;

(e)

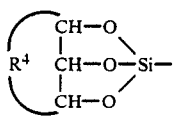

wherein $R^4$ is a straight or branched alkyl moiety of from 2 to 9 carbon atoms, inclusive, or a cyclic alkyl moiety of from 5 to 9 carbon atoms, inclusive, said alkyl moieties are optionally substituted with 1 to 9 hydroxyl groups and 1 amino group;

(f)

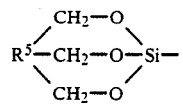

wherein $R^5$ is a straight or branched alkyl moiety of from 1 to 6 carbon atoms, inclusive, optionally substituted with 1 amino group; and $X^\ominus$ is a physiologically acceptable anion.

2. A method for treating swine dysentery in swine in need of such treatment which comprises administering to said swine an animal feed composition comprising animal feed in admixture with an effective swine dysentery treating amount of at least one of the compounds of the formula:

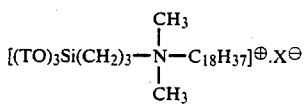

wherein each T independently represents a straight or branched alkyl moiety of from 1 to 5 carbon atoms, inclusive, or a cyclic alkyl moiety of from 3 to 5 carbon atoms, inclusive, said alkyl moieties are optionally substituted with 1 to 5 hydroxyl groups and 1 amino group; and $X^\ominus$ is a physiologically acceptable anion.

3. A method for treating swine dysentery in swine in need of such treatment which comprises administering to said swine an animal feed composition comprising animal feed in admixture with an effective swine dysentery treating amount of at least one of the compounds of the formula:

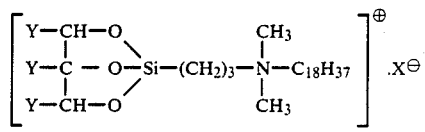

wherein each Y independently represents H, or a straight or branched alkyl moiety of from 1 to 3 carbon atoms, inclusive, optionally substituted with 1 to 3 hydroxyl groups and 1 amino group; and $X^\ominus$ is a physiologically acceptable anion.

4. A method for treating swine dysentery in swine in need of such treatment which comprises administering to said swine an animal feed composition comprising animal feed in admixture with an effective swine dysentery treating amount of at least one of the compounds of the formula:

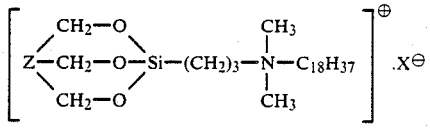

wherein Z represents an alkyl moiety of 1 or 2 carbon atoms optionally substituted with 1 amino group; and $X^\ominus$ is a physiologically acceptable anion.

5. The method of claim 1 wherein $X^\ominus$ is chloride.

6. The method of claim 2 wherein X$^\ominus$ is chloride.
7. The method of claim 3 wherein X$^\ominus$ is chloride.
8. The method of claim 4 wherein X$^\ominus$ is chloride.
9. The method of claim 2 wherein T is ethyl.
10. The method of claim 2 wherein T is ethyl and X$^\ominus$ is chloride.
11. The method of claim 1 wherein R is

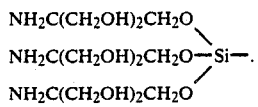

12. The method of claim 1 wherein R is

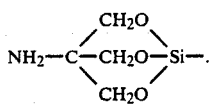

13. The method of claim 1 wherein R is

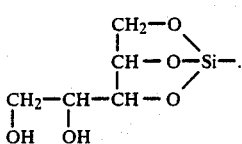

14. The method of claim 1 wherein said effective amount is from about 500 parts by weight of the compound or compounds per million parts by weight of the final animal feed composition (ppm) to about 1,500 ppm.

15. The method of claim 1 wherein said effective amount is from about 600 parts by weight of the compound or compounds per million parts by weight of the final animal feed composition (ppm) to about 1,000 ppm.

16. The method of claim 2 wherein said effective amount is from about 500 parts by weight of the compound or compounds per million parts by weight of the final animal feed composition (ppm) to about 1,500 ppm.

17. The method of claim 2 wherein said effective amount is from about 600 parts by weight of the compound or compounds per million parts by weight of the final animal feed composition (ppm) to about 1,000 ppm.

18. The method of claim 3 wherein said effective amount is from about 500 parts by weight of the compound or compounds per million parts by weight of the final animal feed composition (ppm) to about 1,500 ppm.

19. The method of claim 3 wherein said effective amount is from about 600 parts by weight of the compound or compounds per million parts by weight of the final animal feed composition (ppm) to about 1,000 ppm.

20. The method of claim 4 wherein said effective amount is from about 500 parts by weight of the compound or compounds per million parts by weight of the final animal feed composition (ppm) to about 1,500 ppm.

21. The method of claim 4 wherein said effective amount is from about 600 parts by weight of the compound or compounds per million parts by weight of the final animal feed composition (ppm) to about 1,000 ppm.

22. An animal feed composition which comprises animal feed in admixture with an effective swine dysentery treating amount of at least one of the compounds of the formula:

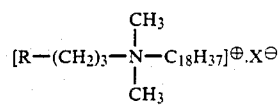

wherein R represents:
(a)

$(R^1O)_3Si-$ wherein each $R^1$ independently represents a straight or branched alkyl moiety of from 1 to 12 carbon atoms, inclusive, or a cyclic alkyl moiety of from 3 to 12 carbon atoms, inclusive, said alkyl moieties are optionally substituted with 1 to 12 hydroxyl groups and 1 to 2 amino groups;

(b)

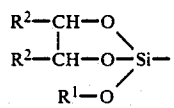

wherein each $R^2$ independently represents H or a straight or branched alkyl moiety of from 1 to 11 carbon atoms, inclusive, or a cyclic alkyl moiety of from 3 to 11 carbon atoms, inclusive, said alkyl moieties are optionally substituted with 1 to 11 hydroxyl groups and 1 to 2 amino groups, and $R^1$ is as defined hereinabove;

(c)

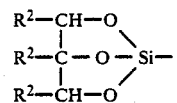

wherein $R^2$ is as defined hereinabove;

(d)

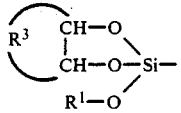

wherein $R^3$ is a straight or branched alkyl moiety of from 3 to 10 carbon atoms, inclusive, or a cyclic alkyl moiety of from 6 to 10 carbon atoms, inclusive, said alkyl moieties are optionally substituted with 1 to 10 hydroxyl groups and 1 to 2 amino groups, and $R^1$ is as defined hereinabove;

(e)

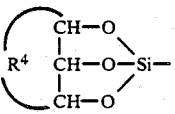

wherein $R^4$ is a straight or branched alkyl moiety of from 2 to 9 carbon atoms, inclusive, or a cyclic alkyl moiety of from 5 to 9 carbon atoms, inclusive, said alkyl moieties are optionally substituted with 1 to 9 hydroxyl groups and 1 amino group; or (f)

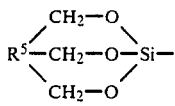

wherein $R^5$ is a straight or branched alkyl moiety of from 1 to 6 carbon atoms, inclusive, optionally substituted with 1 amino group; and $X^\ominus$ is a physiologically acceptable anion.

23. An animal feed composition which comprises animal feed in admixture with an effective swine dysentery treating amount of at least one of the compounds of the formula:

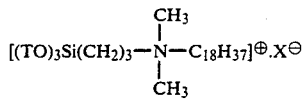

wherein each T independently represents a straight or branched alkyl moiety of from 1 to 5 carbon atoms, inclusive, or a cyclic alkyl moiety of from 3 to 5 carbon atoms, inclusive, said alkyl moieties are optionally substituted with 1 to 5 hydroxyl groups and 1 amino group; and $X^\ominus$ is a physiologically acceptable anion.

24. An animal feed composition which comprises animal feed in admixture with an effective swine dysentery treating amount of at least one of the compounds of the formula:

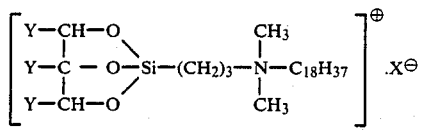

wherein each Y independently represents H, or a straight or branched alkyl moiety of from 1 to 3 carbon atoms, inclusive, optionally substituted with 1 to 3 hydroxyl groups and 1 amino group; and $X^\ominus$ is a physiologically acceptable anion.

25. An animal feed composition which comprises animal feed in admixture with an effective swine dysentery treating amount of at least one of the compounds of the formula:

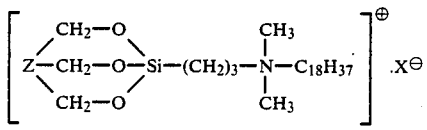

wherein Z represents an alkyl moiety of 1 or 2 carbon atoms optionally substituted with 1 amino group; and $X^\ominus$ is a physiologically acceptable anion.

26. The composition of claim 22 wherein $X^\ominus$ is chloride.
27. The composition of claim 23 wherein $X^\ominus$ is chloride.
28. The composition of claim 24 wherein $X^\ominus$ is chloride.
29. The composition of claim 25 wherein $X^\ominus$ is chloride.

30. The composition of claim 23 wherein T is ethyl.
31. The composition of claim 23 wherein T is ethyl and $X^\ominus$ is chloride.
32. The composition of claim 22 wherein R is

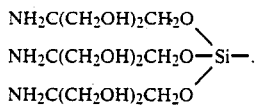

33. The composition of claim 22 wherein R is

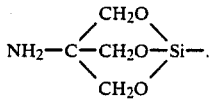

34. The composition of claim 22 wherein R is

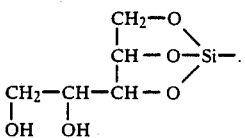

35. The composition of claim 22 wherein said effective amount is from about 500 parts by weight of the compound or compounds per million parts by weight of the final animal feed composition (ppm) to about 1,500 ppm.

36. The composition of claim 22 wherein said effective amount is from about 600 parts by weight of the compound or compounds per million parts by weight of the final animal feed composition (ppm) to about 1,000 ppm.

37. The composition of claim 23 wherein said effective amount is from about 500 parts by weight of the compound or compounds per million parts by weight of the final animal feed composition (ppm) to about 1,500 ppm.

38. The composition of claim 23 wherein said effective amount is from about 600 parts by weight of the compound or compounds per million parts by weight of the final animal feed composition (ppm) to about 1,000 ppm.

39. The composition of claim 24 wherein said effective amount is from about 500 parts by weight of the compound or compounds per million parts by weight of the final animal feed composition (ppm) to about 1,500 ppm.

40. The composition of claim 24 wherein said effective amount is from about 600 parts by weight of the compound or compounds per million parts by weight of the final animal feed composition (ppm) to about 1,000 ppm.

41. The composition of claim 25 wherein said effective amount is from about 500 parts by weight of the compound or compounds per million parts by weight of the final animal feed composition (ppm) to about 1,500 ppm.

42. The composition of claim 25 wherein said effective amount is from about 600 parts by weight of the compound or compounds per million parts by weight of the final animal feed composition (ppm) to about 1,000 ppm.

* * * * *